United States Patent [19]

Geho et al.

[11] Patent Number: 4,942,036

[45] Date of Patent: Jul. 17, 1990

[54] THERAPY BY VESICLE DELIVERY TO THE HYDROXYAPATITE OF BONE

[76] Inventors: W. Blair Geho, 533 Beechwood St.; John R. Lau, 1634 Morgan St., both of Wooster, Ohio 44691

[21] Appl. No.: 236,253

[22] Filed: Aug. 25, 1988

[51] Int. Cl.$^5$ .................. A61F 2/00; A61K 37/22; B01J 13/02

[52] U.S. Cl. ...................... 424/425; 428/402.2; 424/450

[58] Field of Search ............ 428/402.2; 424/450; 436/829

[56] References Cited

U.S. PATENT DOCUMENTS

| | | | |
|---|---|---|---|
| 4,193,983 | 3/1980 | Ullman et al. | 424/450 X |
| 4,501,728 | 2/1985 | Geho et al. | 428/402.2 X |
| 4,544,545 | 10/1985 | Ryan et al. | 424/450 X |
| 4,603,044 | 7/1986 | Geho et al. | 428/402.2 X |
| 4,692,433 | 9/1987 | Hostetler et al. | 424/450 X |
| 4,698,328 | 10/1987 | Neer et al. | 514/12 |
| 4,767,615 | 8/1988 | Geho et al. | 424/57 |

*Primary Examiner*—Matthew A. Thexton
*Assistant Examiner*—John M. Covert

[57] ABSTRACT

A known procedure is used to prepare vesicles consisting of bipolar lipid membranes which are permeable and hence "leak" their contents at a rate which is variable by choice.

The vesicle is supplied with medication or diagnostic material and then attached to a target molecule conjugate that has affinity for the hydroxyapatite of bone.

Thus, the vesicle clings to the skeleton structure and bathes the surrounding support surface with its contents for extended hours.

9 Claims, 3 Drawing Sheets

CLASS OF POLYPHOSPHATES

Pyrophosphate

Adenosine triphosphate

CLASS OF POLYPHOSPHOINOSITIDES

L-α-phosphatidyl inositol-4,5-diphosphate

CLASS OF CARBOXYLIC ACIDS

Mellitic Acid

THERAPY BY VESICLE DELIVERY TO THE HYDROXYAPATITE OF BONE

BACKGROUND OF THE INVENTION

1. Field of the Invention

A chemically-structured delivery system for targeting vesicles containing medication or diagnostic material to the bone structure of a warm-blooded animal.

2. Description of the Prior Art

The biochemistry of the polyphosphoinositides, polyphosphates, polyphosphonates, diphosphonates, and the carboxylic acids, and their derivatives, as noted in the scientific literature, demonstrates that these molecules are capable of participating in chemical reactions that result in the formation of exceptionally strong coordination complexes with the calcium ions of the hydroxyapatite crystal of bone over a very broad pH range. The chemical process of binding vesicles to the hydroxyapatite of bone is one of chemisorption.

For an appropriate description of prior art, please refer to U.S. Pat. No. 4,603,044 (Hepatocyte Directed Vesicle Delivery System).

SUMMARY OF THE INVENTION

This invention resides primarily in the discovery that a lipid vesicle containing a medical or diagnostic material can be made to target to bone using target molecules representative of the classes of compounds consisting of the polyphosphoinositides, polyphosphates, polyphosphonates, diphosphonates, carboxylic acids, and their derivatives, as listed in FIGS. 2 and 3. These target molecules are a component of a target molecule conjugate that enables the lipid vesicle to bind to the hydroxyapatite of bone. Then, by use of known techniques of making lipid vesicles that slowly release entrapped pharmacologic or diagnostic core materials, a supply of such core material is released to the hydroxyapatite of bone over extended time periods.

BRIEF DESCRIPTION

The target molecule conjugate is composed of a connector molecule, a bridging ion, and a terminal targeting moiety that chemisorbs to the surface of bone hydroxyapatite crystals. The lipophilic end of the connector molecule is caused to penetrate the wall of the vesicle and to associate with other lipophilic chains of neighboring liposomal wall constituents, thereby forming weak van der Waals bonds or interactions. The hydrophilic end of the connector molecule is negatively charged and forms bonds to a bridging ion. The terminal targeting moiety is also negatively charged, and thus forms bonds to the same bridging ion. The resultant composition causes the hydrophilic end of the terminal target molecule to form strong ligands with the hydroxyapatite of bone.

Heretofore, effort has been directed to masking vesicles from the reticuloendothelial system (RES) in order to provide extended circulation time. The invention provides a molecule that attaches to the skeleton and anchors the target conjugate which is attached to the vesicle. The vesicle delivery system can be masked from the site of the RES. Thus, by masking the vesicle from the RES, and the vesicle survives for an extended time during which the contained medication of diagnostic material leaks to the support structure for therapeutic purposes. In some instances it is desirable to mask the vesicle from the RES as disclosed by prior art. Please refer to U.S. Pat. No. 4,501,2728 (Masking of Liposomes from RES Recognition).

DEFINITIONS

Vesicle: A substantially spherical thin-walled bladder, usually ranging in size from 250 Å to 1500 Å.

Liposome: A larger spherical bladder, often of layered walls, ranging in size from about 1000 Å to several microns.

Existing literature makes no practical or consistent distinction between "vesicle" and "liposome." Therefore, for the purpose of this teaching and for the sake of clarity, "vesicle" is understood to refer also to liposomal bladders.

For the purpose of this teaching, a target conjugate molecule is a composite chemical structure, such as that depicted in FIG. 1, with two separate molecules joined by a bridging ion. The preferred structure, as illustrated, is composed of a molecule which has a lipophilic and hydrophilic component. The hydrophilic moiety exhibits chemisorption bonding to the hydroxyapatite of bone.

DESCRIPTION OF THE PREFERRED EMBODIMENT

The primary object of this invention is to provide a sustained release mechanism for medical and diagnostic materials contained in the lipid vesicle delivery system that binds to the hydroxyapatite of bone.

The vesicle is made permeable to allow the material contained in the core volume to leak slowly from the vesicle and to provide a continuous supply of material to the body or skeleton for an extended period of time.

For a definitive explanation of how vesicles are made, see U.S. Pat. No. 4,603,044 (Hepatocyte Directed Delivery System.)

See also, Kitagawa, Inoue, and Mojima, "Properties of Liposomal Membranes Containing Lysolecithin", *J. Biochem.*, 79 1123–1133 (1976); Papahadjopoulos and Watkins, "Permeability Properties of Hydrated Liquid Crystals," *Biochem. Biophs. Acta* 135 (1967), 639–652; and Bittman et al., "Chemistry and Physics of Lipids," 28 (1981) 323–34, Elsevier/North Holland Scientific Publishers, Ltd., as teaching of permeable vesicle technique.

Using this type of vesicle, applicant observed objectively that the treatment and diagnostic materials adhered to the hydroxyapatite of bone.

According to this invention, the polyphosphoinositides, diphosphonates, polyphosphonates, polyphosphates, carboxylic acids, and their derivatives listed in Table 1 are utilized for targeting and subsequent binding of lipid vesicles to the hydroxyapatite of bone.

For example, the vesicle delivery system utilizing the membrane connector molecule L-α-phosphatidylinositol-4,5-diphosphate allows the connector to function two ways. First, the connector molecule bonds to the bridging ion while also anchoring the entire target conjugate to the vesicle membrane. Alternatively, the connector molecule functions both as a connecting molecule and a terminal target molecule since its negatively charged phosphate groups bind directly to the hydroxyapatite of bone at physiological pH.

Moreover, since the polyphosphoinoisitides such as L-α-phosphatidylinositol-4,5-diphosphate are naturally occurring phospholipids with hydrophilic polyphospoinositol head groups and hydrophobic fatty acids tail groups, they are uniquely suited for incorporation into vesicle membranes.

A general definition of the invention is as follows: the discovery that a permeable, or "leaky," vesicle is attached to a bone surface by means of a target conjugate for the purpose of supplying medication or diagnostics to a warm-blooded animal. At one end, the target conjugate is lipophilic and thus held by van der Waals forces in the lipophilic membrane of the vesicle. At the other end, the target conjugate is hydrophilic and has an affinity for the hydroxyapatite of a bone surface. Such a structure, comprised of the fragile vesicle and its target conjugate, binds to the hydroxyapatite of a bone surface for an extended period of time, thereby permitting the contents of the vesicle to bath the bone surface more efficiently than any technique known prior to this invention.

Figure 1:
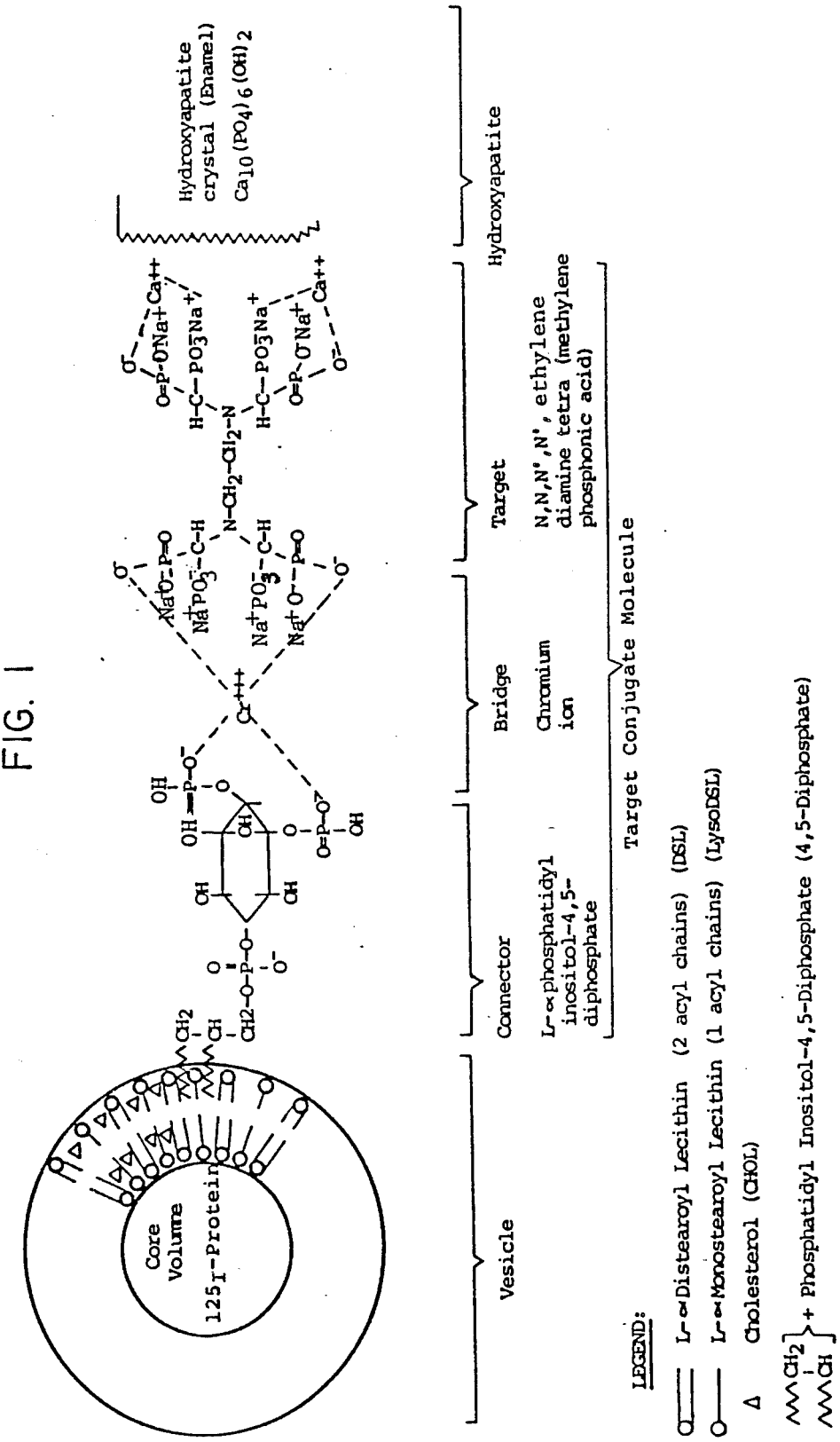
FIG. 1 is a structural representation of a unilamellar vesicle carrying a core volume of radioactive tracer material for delivery to bone hydroxyapatite, and a target conjugate molecule linking the vesicle to the bone hydroxyapatite.
Figure 2:
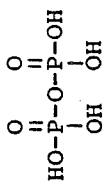
FIGS. 2 and 3 list target molecules representative of the chemical classes which include the polyphosphoinositides, polyphosphates, polyphosphonates, diphosphonates and carboxylic acids.
Figure 2:
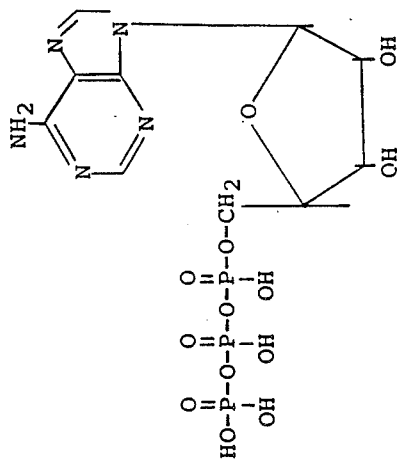
Figure 2:
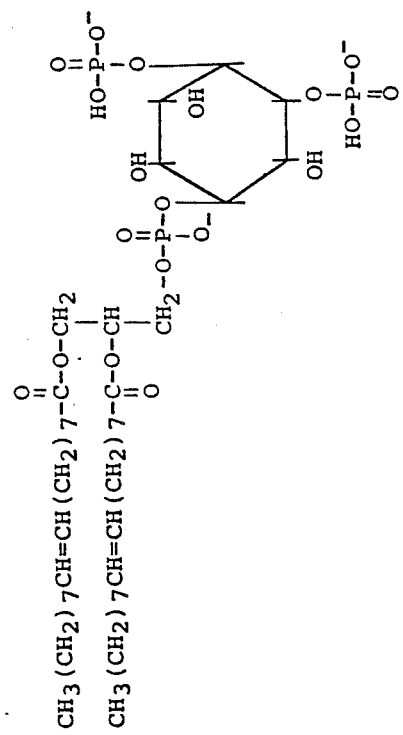
Figure 2:
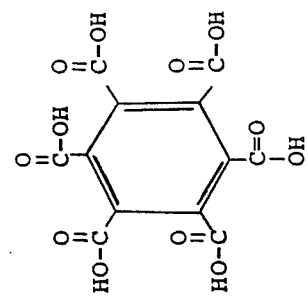
Figure 3:
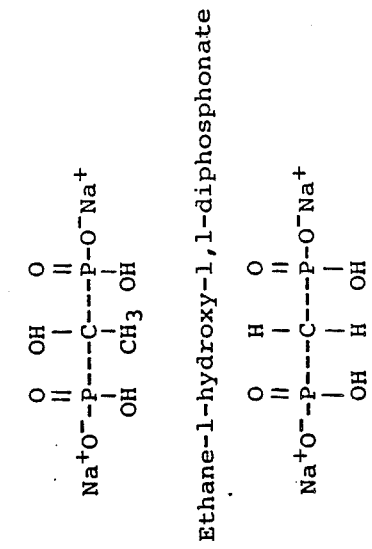
Figure 3:
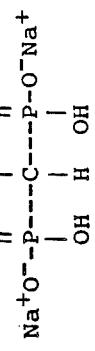
Figure 3:
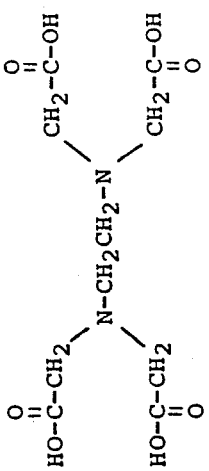
Figure 3:
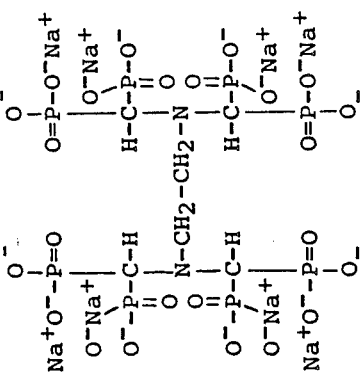

FIG. 1 illustrates the preferred embodiment of the above-described invention and depicts the target conjugate molecule as the preferred means to target the vesicle to the bone surface. The portion of the conjugate labelled "connector" is amphipathic; one moiety is hydrophobic, or lipophilic, held by van der Walls attraction in the vesicle's lipid membrane. The other end of the connector is hydrophilic and terminates in phosphate ions. The portion of the target conjugate labelled "target" also terminates in phosphate ions which are attracted to and sandwiched between the calcium ions of the hydroxyapatite by chemisorption. This terminal target moiety has, at the other end, phosphate ions containing oxygen atoms which are connected by bonding forces to a chromium "bridging ion." The chromium bridging ion connects the phosphates of the connector molecule and the phosphates of the target molecule, by completing the target conjugate structure.

It is important to note that the connector moiety L-α-phosphatidylinositol-4,5-diphosphate bonds directly to the hydroxyapatite without the necessity of the target and bridging ion illustrated. However, FIG. 1 illustrates the preferred embodiment of this invention.

DELIVERY SYSTEM PREPARATION

The synthetic procedure for the preparation of the targeted bone delivery system is described as follows: 28.96 mg of L-disteraroyl lecithin and 1.67 mg of cholesterol, for the formation of a bipolar vesicle, plus 1.40 mg of L-α-phosphatidylinositol-4,5-diphosphate, the connector molecule, are solubilized in chloroform:methanol (2:1 v/v) and dried under house vacuum for 15 minutes at 60° C. ±0.5° C. to form a lipid crust. The lipid constituents are then sonicated in the cuphorn at 60° C. ±0.5° C. for 15 minutes at setting #4 on the sonicator. The sample is then annealed with slow turning at 60° C. ±0.5° C. for 15 minutes. Following the annealing step, the sample is centrifuged in the Triac Clinical Centrifuge on the bloodsetting mode at ambient temperature for 15 minutes. The supernatant containing the lipid suspension is chromatographed over a 1.5 cm × 25 cm Sephadex G-100-120 column that has been equilibrated with 40 mM $K_2HPO_4$—$KH_2PO_4$ pH 7.4 phosphate buffer.

TEST PROCEDURE

The following experiment demonstrates the high affinity of boneseeking vesicles for the hydroxyapatite of bone.

Vesicles were constructed of lecithin and cholesterol with a polyphosphonate terminal target molecule for bone, as shown in FIG. 1. The vesicles were labelled with $^{125}I$-protein contained within the core volume of the vesicle. These vesicles were made by the sonication method and were chromatographed using Sephadex G-100-120 gel filtration techniques to remove the untrapped protein from the vesicles.

Three adult, female, intact Charles River CD rats, weighing 200 grams, were used. The radio-labelled vesicle (100 ul containing 47,000 counts of $^{125}I$ per two minutes) were administered subcutaneously. At one hour, the three rats were euthanized with $CO_2$ gas, and various tissues were removed and counted in an Abbott Gamma Counter for two minutes. The samples selected for study were bone, liver, spleen, heart, lungs, kidneys, and skin.

At two hours, the calculated percent doses in the above-selected samples were as follow:

| Tissue | | Percent |
| --- | --- | --- |
| Bone | | 28% |
| Liver | | 1% |
| Spleen | | 1% |
| Muscle | | 4% |
| Heart | less than | 1% |
| Lungs | less than | 1% |
| Skin | | 4% |
| Kidneys | | 1% |
| Injection site | | 5% |

From these data, it was concluded that the bone-seeking vesicles had a high affinity for bone as compared to the usual soft-tissue sites of vesicle accumulation, e.g., liver and spleen.

What is claimed is:

1. The method of providing a continuous supply of chemicals to the body or skeleton of a warm-blooded animal for extended periods of time, comprising preparation of targeted, permeable, bipolar, lipid vesicles containing said chemicals, said targeted lipid vesicles having affinity for the hydroxyapatite of bone, and administering said targeted vesicles to the internal body compartments of said animal.

2. The method of claim 1 wherein a targeted conjugate molecule is the targeted member for the vesicle and is attached to each of said vesicles, said targeted conjugate molecule characterized by having a connector lipid substituent in the vesicle wall and a bridging substituent between the connector lipid substituent and a terminal target molecule.

3. The method of claim 2 wherein said terminal target molecule comprises a member selected from the class consisting of the polyphosphoinositides.

4. The method of claim 2 wherein said terminal target molecule comprises a member selected from the class consisting of the polyphosphates.

5. The method of claim 2 wherein said terminal target molecule comprises a member selected from the class consisting of the polyphosphonates.

6. The method of claim 2 wherein said terminal target molecule comprises a member selected from the class consisting of the diphosphonates.

7. The method of claim 2 wherein said terminal target molecule comprises a member selected from the class consisting of the carboxylic acids and system of claim 2.

8. The method of claim 1 wherein said bipolar lipid vesicle provides a sustained-release mechanism for supplying medical and diagnostic materials to the body or skeleton of a warm-blooded animal comprising:
    a. bipolar lipid vesicle having a chemical composition exhibiting permeability with entrapped medical and diagnostic material therein and whereby at least one terminal target molecule exhibiting strong ligands characterized by chemisorption to the hydroxyapatite of bone; and whereby contained material of the vesicle is released to the treatment area for an extended time period.

9. The method of providing a continuous supply of chemicals to the body or skeleton of a warm-blooded animal or extended periods of time, comprising preparation of targeted, permeable, bipolar, lipid vesicles containing said chemicals, said targeted lipid vesicles comprising the class of polyphosphoinositides attached directly to said vesicle wall and having affinity for the hydroxyapatite of bone, and administering said vesicles to the internal body compartments of said animal.

* * * * *